United States Patent [19]

Le Maitre et al.

[11] 4,078,554
[45] Mar. 14, 1978

[54] SPIROMETRIC DEVICE

[75] Inventors: André Emmanuel Le Maitre, Saint Maur; Roger Paul Charles Cavallo, Bourg la Reine, both of France

[73] Assignee: Synthelabo, Paris Cedex, France

[21] Appl. No.: 723,343

[22] Filed: Sep. 15, 1976

[30] Foreign Application Priority Data

Sep. 18, 1975 France ................................. 75 28561

[51] Int. Cl.² .............................................. A61B 5/08
[52] U.S. Cl. ..................................... 128/2.08; 73/198
[58] Field of Search ................. 128/2.08, 2.07; 73/198

[56] References Cited

U.S. PATENT DOCUMENTS

| 3,006,336 | 10/1961 | Burlis et al. | 128/2.08 |
| 3,605,729 | 9/1971 | Liu et al. | 128/2.08 |
| 3,759,249 | 9/1973 | Fletcher | 128/2.08 |
| 3,799,149 | 3/1974 | Rummet et al. | 128/2.07 |
| 3,946,729 | 3/1976 | Hanna | 128/2.08 X |

FOREIGN PATENT DOCUMENTS 474,996  8/1969  Switzerland ..................... 128/2.08

OTHER PUBLICATIONS

Murphy et al., "A Dynamic Compliance Computer:... . Man", J. Applied Physiology, vol. 36, No. 5, May 1974, pp. 629–633.

Primary Examiner—Robert W. Michell
Assistant Examiner—Lee S. Cohen
Attorney, Agent, or Firm—Sughrue, Rothwell, Mion, Zinn and Macpeak

[57] ABSTRACT

A spirometric device for connection to the respiratory piping system of a patient and wherein a delivery pickup system is situatable on an exhalation branch of the system. The signals transmitted by a pressure pickup included in the device and situated on the respiratory system and those transmitted by the delivery pickup are led to a computing and measuring assembly which integrates the delivery signals while correcting these as a function of the pressure variations and/or of the errors caused by the gas contained in the respiratory system.

6 Claims, 4 Drawing Figures

SPIROMETRIC DEVICE

The present invention relates to a spirometric device incorporating pressure correction, applicable in particular to controlled delivery respirators, that is to say to an apparatus allowing a patient to be induced to breathe artificially. The spirometric device measures the volume or the delivery of gas exhaled, referred to as "current volume," the same substantially corresponding to the respiratory capacity, referred to as the "effective" capacity hereinafter, since it corresponds to the quantity of gas the lungs may actually exhale and which is evidently smaller than the true capacity, the lungs not emptying altogether during each breathing cycle up to the point of collapse.

In the prior art a variety of artificial respiratory techniques have been employed without yielding complete satisfaction; the following patents will be cited by way of example:

U.S. Pat. No. 3,006,336 filed on July 26, 1957. In accordance with this patent, the device to nullify the pressure loss in the spirometer which impedes the exhalation of the patient, by means of a piston controlled in such manner as to keep the pressure constant in the chamber of the spirometer.

The prior art moreover comprises many devices for measuring volumes of volumetric flows incorporating pressure correction, making use of a pressure correction by application of Boyle's law, and in particular U.S. Pat. Nos. 3,759,249 and 3,799,149 which, respectively, relate to a respiratory analysis device incorporating a mass spectrometer and a metabolic analyzer wherein a calculator introduces a pressure correction by application of Boyle's law.

The fact that the pressure is controlled and measured is disclosed in U.S. Pat. No. 3,414,896 filed on Jan. 5, 1965.

Practically all the known devices operate on an approximate pressure measurement and do not allow for the variations of this pressure, which are frequently substantial during one and the same cycle.

According to the present invention there is provided a spirometric device for connection to a respiratory piping system of a patient and comprising a delivery pickup system for location on an exhalation branch of the system and responsive to signals transmitted thereby, a pressure pickup situated on said system and responsive to signals transmitted thereby, and pressure pickup signals being fed to a computing and measuring assembly for integrating the delivery signals and correcting these as a function of pressure variations, said pressure pickup being followed by two circuits in parallel for detecting the maximum pressure and the minimum pressure and by a first subtracting device for delivering an analogical signal proportional to the difference of said two extreme pressures.

With the device of the present invention, the measurement is rendered more precise while making allowance for the maximum pressure and the minimum pressure as well as for the overpressures or negative pressures occurring during the respiratory cycle.

Moreover, the solution offered by the present invention is very uncomplicated and, as compared to other solutions such as the mechanical solution of U.S. Pat. No. 3,006,336, offers the advantages of electronics which are now well known.

The invention will now be described by way of example with reference to the accompanying drawings wherein.

The corresponding elements of the different figures are marked by the same references. In these figures, it is assumed that there is a negative pressure. If there is no negative pressure, it is sufficient to replace the indices 2 by the indices 0.

Figure 1:
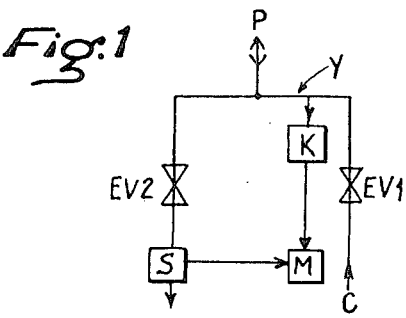
FIG. 1 shows a conventional artificial respiration system.

It is appropriate to recall, with reference to FIG. 1, that a conventional artificial respiration apparatus essentially comprises a Y-shaped pipe whereof one branch is connected to the patient P, a second one to a source of gas under pressure (bottle or tank and compressor, in particular) via a valve EV1 which is commonly electrical in recent equipment, and the third to the surrounding atmosphere via a valve EV2, which is equally electrical in the greater number of cases, followed or not by a spirometer S.

It is known that when the patient requires artificial respiration, that is to say if it is thought that he is partly or wholly unable to ensure his own breathing spontaneously, so that upon inhalation (EV2 being closed and EV1 being open) the patient should be subjected to a slight overpressure as compared to atmospheric pressure, this overpressure being increased the more difficult the patient's own breathing. The volume inhaled is thus at a pressure differing from the atmospheric pressure prevailing externally, which corresponds to a gaseous mass greater than that of an identical volume at atmospheric pressure. Moreover upon exhalation (EV1 being closed, and EV2 being open), the pressure is reestablished progressively and the pressure of the air varies as it is being discharged through the spirometer, that is to say that the initial overpressure diminishes until it is zero, so that the spirometer measures a volume under a pressure varying in the course of the operation.

The effect of the overpressure on the volume, in the case in which it is itself negligible, may be ignored, but it must normally be taken into account.

The present invention offers a solution to this problem by means of a pickup K measuring the pressure in the Y pipe, with data transmitted to a measuring and computing unit M which, equally receiving the data from the spirometer S, and instantaneously applies the required corrections to the measurements of this latter. If the index 0 is attributed to the atmospheric conditions and the index 1 to the maximum overpressure conditions (which may possibly vary from one respiratory cycle to another) M thus no longer integrates the volumes passing into the spirometer, but these volumes are corrected to atmospheric pressure.

As will be apparent from the two examples of embodiment described below, two solutions are offered, the one being approximative, wherein the delivery is integrated for multiplication by the pressure variation $$\frac{P_1 - P_0}{P_0} \int_1^0 dV,$$

the other being more precise, wherein the flow corrected for atmospheric pressure is integrated at each instant $$\int_1^0 \frac{P}{Po} \, dV,$$

P being the momentary pressure measured by the pickup K, the momentary elementary volume $dV$ or the momentary delivery $dV/dt$ being measured by Boyle's law, which is applicable for perfect gases or for real gases for low pressure variations, which is the most common case in spirometry, is applied in the present case, but it would be possible to integrate while applying another law in extreme cases, that is to say if the pressure variations were to be very substantial. This is possible, for example, when victims of dives to great depths are being revived in a pressurized chamber.

Allowance should equally be made for the fact that, on modern equipment, not only is the operation performed under overpressure upon inhaling, but equally under negative pressure upon exhaling (index 2);

$$\frac{P1 - P2}{Po} \int_1^2 dV \text{ or } \int_1^2 \frac{P}{P1} \, dV,$$

is thus integrated in M. Corrections may also be made if the spirometer itself causes a pressure loss damping the pressure variations in the course of time.

What is more, it is appropriate to recall that the volume of the ducts is not negligible as a rule and that it must be taken into account since the datum of importance to the doctor is the quantity of gas discharged by the lungs. This information may be available without correction at the mouth of the sick person by measuring the delivery and pressure at the same, but this localization of the measurements is inappropriate because of the fouling caused by the condensations of water vapour or the excretions of the patient, which falsifies the measurements. This explains why, at this time, the trend is to position the pickups, particularly those intended for the rate of flow, sufficiently far from the mouth of the sick person, so that the result thereof is an increase in length and volume of the pipes which must be taken into account.

Consequently, it is appropriate to reduce the volume at atmospheric pressure corresponding to the gaseous mass which, itself, corresponds to the difference between those contained in the pipe between P1 and Po.

The delivery pickup S (FIGS. 1 and 2) transmits the flow datum in liters to the unit M during the exhalation periods of each cycle, for example by transmitting a number of pulses proportional to the speed of passage in the pickup and thus proportional to the rate of flow. For example, this may be obtained with a capacitative type turbine pickup.

In integrator 2, the integration as a function of time for each cycle yields the so-called "current volume" volume. In integrator 3, it yields the so-called "minute volume" for each minute. These data correspond to the total volume delivered by the respirator (at varying pressure during a cycle).

The capacity of the pipes being Co notwithstanding the pressure P, a volume $$C = Co \frac{P1}{Po} - Co,$$

that is to say $$\Delta C = Co \frac{(P1 - P0)}{Po}$$

if there is no negative pressure upon exhalation, and $$\Delta C = \frac{CoP1 - CoP2}{Po},$$

that is to say $$\Delta C = \frac{Co(P1 - P2)}{Po},$$

if the contrary is the case, flows within the delivery pickup apart from the respiratory volume.

(The volume Co of the gas in the pipes is actually Co (P/Po) upon changing from the pressure P to the pressure Po).

The pressure pickup K supplies the unit M at 4 with a pressure measurement whereof the maximum P1 is marked at 5 and the minimum (Po or P2 depending on whether there is negative pressure or not) is marked at 6, and the difference is established in 7.

This pressure change is transmitted to the corrector devices 8 and 9 which, respectively receiving the "minute volume" and the "current volume" from 3 and from 2, supply the corrected "minute volume" and the "current volume," with allowance for the pressure variations and for the correction $\Delta C$. The indication is made at 10 and 11, respectively.

Figure 4:
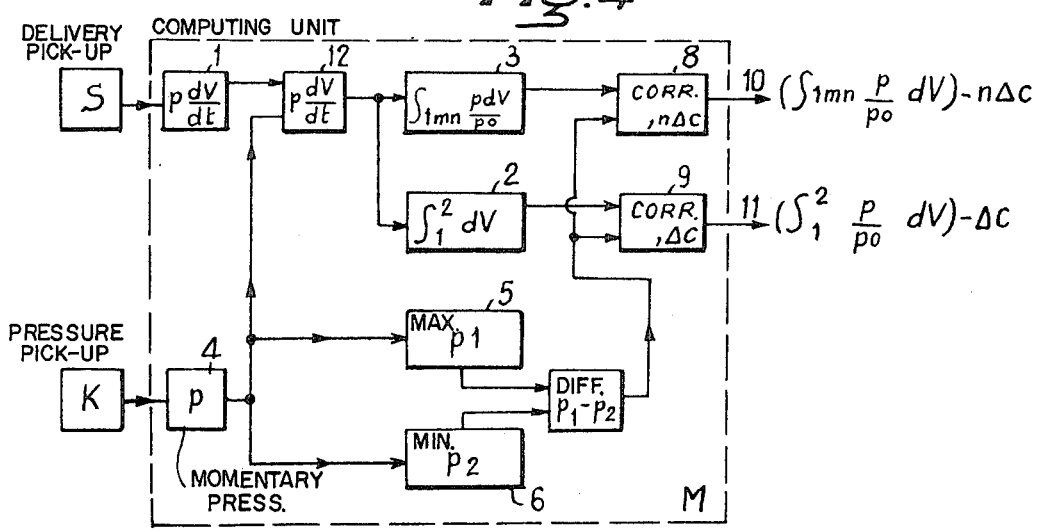

By way of example, this device has been simplified since it does not perform the integration $$\int_1^2 \frac{P}{Po} \, dV \text{ but } \frac{P1 - P2}{Po} \int_1^2 dV = \frac{P1 - P2}{Po} V_1^2,$$

in which $V_1^2$ represents the volume passing into the pickup between 1 and 2, that is to say during the exhalation period. By contrast (FIG. 4) if the momentary pressure P is transmitted from 4 to an instantaneous corrector 12 upflow of the integrators 2 and 3, the integration is then performed as stated above and the computing calculators 2 and 3 deliver $$\int_1^2 \frac{P}{Po} \, dV;$$

the correctors 8 and 9 provide only the correction applicable to $\Delta C$ in this case.

Figure 3:
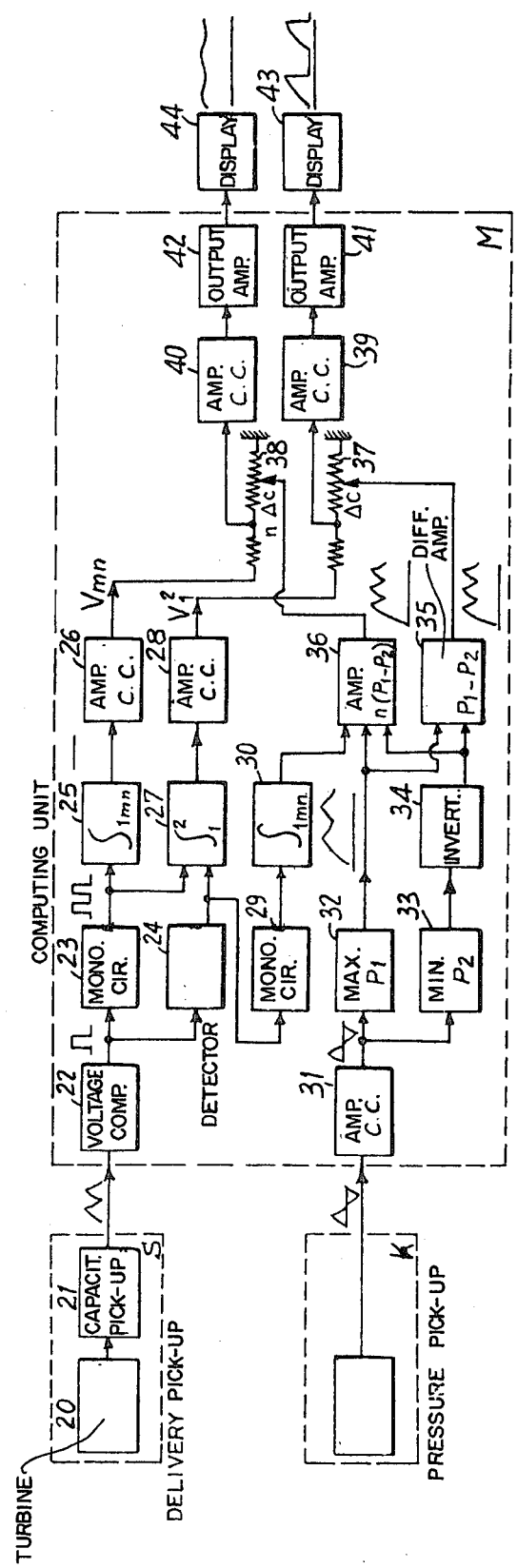
FIG. 3 illustrates a block diagram of the embodiment of FIG. 2.

With reference to FIG. 3, the manner in which circuits performing these operations may be designed, will be understood. If the $\Delta C$ correction is applied for the current volume, the correction $n\Delta C$ will have to be applied for the minute volume, $n$ being the number of respiratory cycles per minute. The measurement of $n$ is not illustrated in diagrams 2 and 4, but an example of embodiment thereof will be given in FIG. 4.

Numerous solutions are actually possible: $n$ is the number of pressure cycles and may thus be counted in K (every time $P = Po$ if there is no negative pressure, or half the number of times when $P = Po$ or P2 are a minimum), or in S every time the delivery becomes nought (inhalation), this solution having the merit of being easy to apply. It is also possible to count the closings and openings of EV1 or EV2; or else to establish the quotient of the "minute volume" and of the "current volume," etc.

Figure 2:
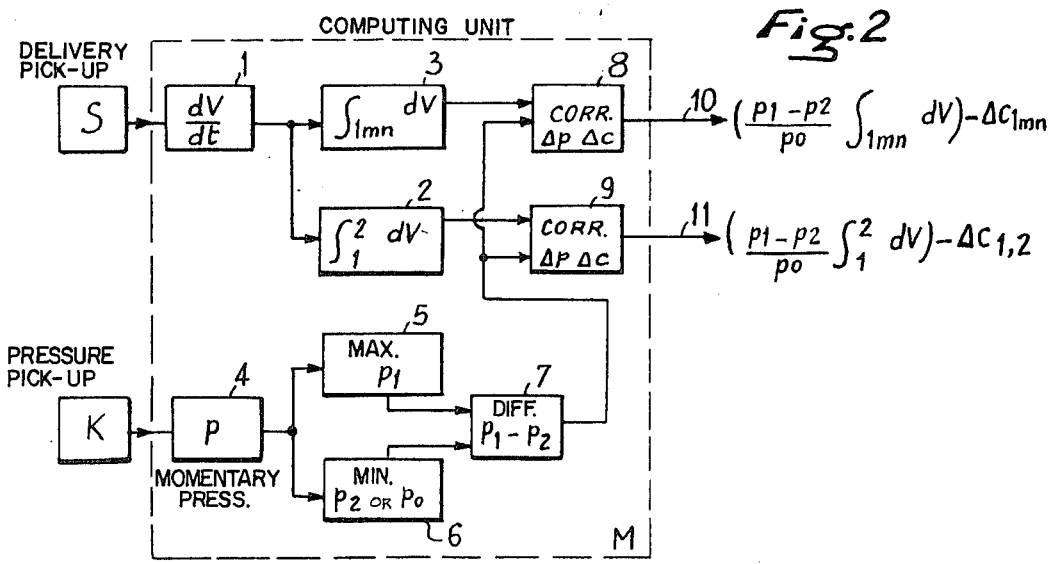
FIGS. 2 and 4 illustrate two versions of fundamental diagrams of the measuring and computing unit M of FIG. 1.

FIG. 3 illustrates an example of embodiment of the fundamental layout of FIG. 2.

With reference to FIG. 3, the greater number of the circuit elements are identical and the transposition lies within the sphere of one versed in the art. The spirometer is constructed by means of a turbine 20 followed by a capacitative pickup 21 and by a voltage comparator 22. The form of the signals transmitted has been illustrated diagrammatically in the figure.

The comparator 22 acts, on the one hand, on a monostable circuit 23 of the constant amplitude pulse type and, on the other hand, on a detector 24 comprising an RC circuit pulse blocked for zero resetting. The signals of the monostable circuit 23 are transmitted, on the one hand, to an RC circuit areal integrator 25 over a minute, followed by a d.c. amplifier 26 which thus delivers an analogical signal proportional to the "minute volume." The signals of the monostable circuit 23 are transmitted, on the other hand, to the RC circuit areal integrator 27 over a cycle, equally followed by a d.c. amplifier 28 transmitting an analogical signal proportional to the "current volume." The integrator 27 acting over one cycle is equally acted upon by the detector 24 which resets the integrator 27 to zero for each cycle and triggers the monostable circuit 29 of the constant amplitude pulse type, followed by an areal integrator 30 acting over one minute, which consequently transmits a signal proportional to $n$, the respiratory frequency per minute.

Moreover, the analogical pressure pickup K is followed by a d.c. amplifier 31 followed by a filter 32 separating the crests P1 and in parallel by a filter 33 separating the troughs (or negative crests) P2 (or $Po$).

P2 is inverted in 34 which renders it possible, on the one hand, to summate P1 − P2 in the amplifier 35 from the signals issuing from 32 and 34 and, on the other hand, to establish $n$(P1 − P2) in the amplifier 36 from the signals issuing from 30; the amplifiers 35 and 36 thus deliver analogical signals proportional, respectively, to $\Delta C_1^2$ and $\Delta C1$ min. The signals issuing from the summating amplifiers 35 and 36 are adjusted by means of the potentiometers 37 and 38, respectively, to allow for the true volume of the pipes which may evidently vary according to the conditions of application. The d.c. amplifiers 39 and 40 respectively, will thus receive analogical signals corresponding to $\Delta C_1^2$ and $\Delta C1$ min. originating from 37 and 38 and analogical signals corresponding to $V_1^2$ and $V_1$min. originating from 28 and 26. They correct the volumes and deliver corrected volume signals $V_1^2 - \Delta C_1^2$ and $V\,1$ min $- \Delta C\,1$ min. These amplifiers 39 and 40 are followed, respectively, by output amplifiers 41, 42; the indication may be made by any adequate means, either by analogical indications such as graduated galvanometers 43 and 44, or by digital indications, for example of the "nixies" type.

It will be observed that, in the block diagram of FIG. 3, only the correction of $\Delta C$ has been illustrated, to simplify matters, since the correction of $\Delta p$ is negligible as compared to that of $\Delta C$ in many cases.

We claim:

1. A spirometric device for connection to a respiratory piping system of a patient comprising: a delivery pickup means for location on an exhalation branch of the system and responsive to signals transmitted thereby to generate delivery signals proportional to rate of flow, a pressure pickup means for situation on said system and responsive to signals transmitted thereby to generate pickup signals, a computing and measuring means for integrating the delivery signals and correcting the integrated output as a function of pressure variations to supply a corrected signal, parallel circuit means responsive to said pressure signals for detecting the maximum pressure and the minimum pressure, first subtracting means for obtaining an analogical signal proportional to the difference of said maximum and minimum pressures, and means for supplying the output of said first subtracting means to said computing and measuring means for correcting said integrated output.

2. A device according to claim 1, the computing and measuring means including second subtracting means for subtracting from the integrated signal obtained in the computing and measuring means, the analogical signal proportional to the difference of said maximum and minimum pressures, to thereby correct the measurement as a function of surplus gas volume corresponding to the volume difference of the gas contained in the respiratory system at extreme pressures, when said surplus gas is returned to atmospheric pressure.

3. A device as claimed in claim 2, wherein the first substracting means includes an inverter coupled to one of the parallel circuit means and summation means coupled to said inverter and the other of said parallel circuit means.

4. A device as claimed in claim 3, further including a potentiometric means interposed between said first and second subtracting means to permit adjustment of the pressure difference signal and render said difference signal proportional to the volume of the respiratory system being monitored.

5. A device according to claim 4, wherein said computing and measuring means includes first and second integrators disposed in parallel, the first of said integrators integrates over a given period, and the second of said integrators over a respiratory cycle, dectector means for resetting said second integrator to zero by the signal transmitted by the delivery pickup means, the two integrators being coupled to said second subtracting means, and a multiplier means for multiplying the said signal of the difference of the maximum and minimum pressures by the number of cycles during a given period and means for supplying the multiplied signal to the second subtracting means.

6. A device according to claim 5, further including means for deriving said number of cycles during said given period by counting the zero reset pulses transmitted by the detector means.

* * * * *